United States Patent [19]

Bouchaudon et al.

[11] 3,975,385
[45] Aug. 17, 1976

[54] 7-TRICHLOROACETAMIDO-3-DESACETOXY-CEPHALOSPORANIC ACID ESTERS

[75] Inventors: Jean Bouchaudon, Morsang-sur-Orge; Pierre Le Roy, Thiais; Mayer Naoum Messer, Bievres, all of France

[73] Assignee: Rhone-Poulenc S.A., Paris, France

[22] Filed: Sept. 5, 1974

[21] Appl. No.: 503,274

[30] Foreign Application Priority Data
Sept. 6, 1973  France .................... 73.32150
Mar. 12, 1974  France .................... 74.08378

[52] U.S. Cl. ................. 260/243 C; 260/239.1
[51] Int. Cl.² .............. C07D 501/22; C07D 501/10
[58] Field of Search ................ 260/243 C

[56] References Cited
UNITED STATES PATENTS
3,555,017  1/1971  Bickel et al. .................... 260/243 C
3,591,585  7/1971  Hatfield ........................ 260/243 C Primary Examiner—Paul M. Coughlan, Jr.
Attorney, Agent, or Firm—Stevens, Davis, Miller & Mosher

[57] ABSTRACT

The invention provides 7-trichloroacetamido-3-desacetoxy-cephalosporanic acid derivatives of the formula:

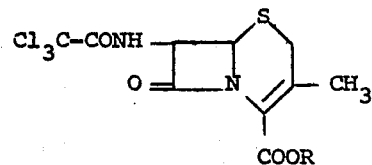

wherein R is a group which protects the carboxylic acid radical, which can be converted into 7-amino-3-desacetoxycephalosporanic acid by replacing the R— and Cl₃C—CO— radicals by hydrogen atoms.

4 Claims, No Drawings

7-TRICHLOROACETAMIDO-3-DESACETOXY-CEPHALOSPORANIC ACID ESTERS

This invention relates to 7-trichloroacetamido-3-desacetoxy-cephalosporanic acids, and to the preparation and use thereof.

The present invention provides 7-trichloroacetamido-3-desacetoxy-cephalosporanic acids of the formula:

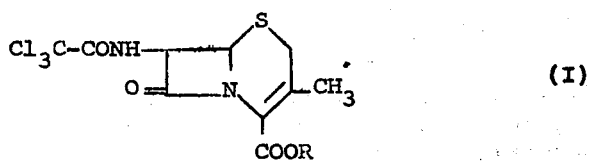

wherein R is a carboxylic acid protecting group such as an alkyl group of 1 to 4 carbon atoms, substituted or unsubstituted by halogen, e.g. chlorine, benzyl, substituted or unsubstituted by nitro or alkoxy of 1 to 4 carbon atoms; e.g. methyl, tertiary butyl, 2,2,2-trichloroethyl, benzyl, p-methoxybenzyl, or p-nitrobenzyl, or phenacyl.

Examples of the compounds of formula (I) are:
3-methyl-8-oxo-7-trichloroacetamido-2-trichloroethoxycarbonyl-5-thia-1-aza-bicyclo[4,2,0]oct-2-ene,
2-p-methoxybenzyloxycarbonyl-3-methyl-8-oxo-7-trichloroacetamido-5-thia-1-aza-bicyclo[4,2,-0]oct-2-ene.

According to the present invention, the compounds of the formula (I) are prepared by one of the following processes:

1. Rearrangement of a sulphoxide of the formula:

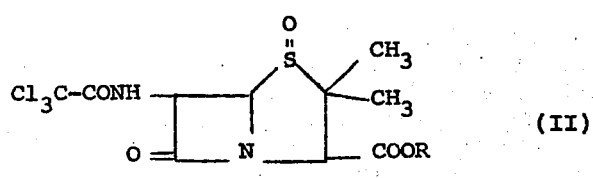

wherein R is as defined above, usually by heating the sulphoxide in an anhydrous acid medium.

The sulphoxide is preferably heated in an inert organic solvent such as dimethylacetamide, dioxane, benzene or a mixture thereof, in the presence of an organic or inorganic acid or an acid salt thereof such as methanesulphonic acid, benzenesulphonic acid, phosphoric acid or pyridinium monophosphate, at the reflux temperature of the reaction medium, whilst removing the water formed during the reaction.

2. Substitution of the $R_1CO-$ group of a compound of the formula:

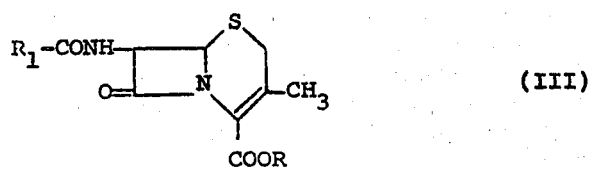

wherein R is as defined above and $R_1$ represent a benzyl or phenoxymethyl group, by a trichloroacetyl group.

This substitution can be performed by reacting the compound of formula (III) with trichloroacetic acid or a functional derivative thereof; i.e. a compound formed by replacement of the hydroxyl group of the acid by some other group that can be hydrolysed back to the parent acid, e.g. the acid halide or anhydride. Trichloroacetyl chloride is preferably used. The reaction is usually performed in a basic organic solvent such as pyridine, at a temperature of between $-20°$ and $+10°C$.

The substitution can also be performed by reacting the iminochloride of a compound of formula (III) with an alkali metal salt of trichloroacetic acid, such as potassium trichloroacetate. The reaction is preferably performed at a temperature of about 20°C, using a solution of the trichloroacetic acid salt in an inert organic solvent such as acetonitrile.

3. When R is an electron-attracting group, such as a 2,2,2-trichloroethyl, p-nitrobenzyl or phenacyl group, cyclising, in an basic medium, a disulphide of the formula:

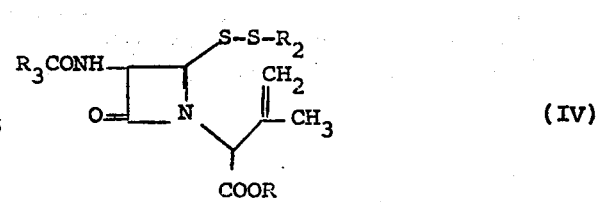

wherein R is an electron-attracting, carboxylic acid protecting group, $R_2$ is a substituted or unsubstituted aryl group or a substituted or unsubstituted aromatic heterocyclic group containing one or more heteroatoms such as oxygen, nitrogen or sulphur, and $R_3$ is a trichloromethyl, benzyl or phenoxymethyl group; and then, when $R_3$ is a benzyl or phenoxymethyl group, replacing the $R_3CO-$ group by a trichloroacetyl group.

The cyclisation is performed in a polar organic solvent, in the presence of a compound which acts as a weak base and it is possible for a single compound to be both the polar organic solvent and the weak base, e.g. N-methylpyrrolidone. The reaction temperature is preferably between $-50°$ and $+30°C$.

Examples of preferred compounds which act as weak bases in a polar solvent are alkali metal or alkaline earth metal salts of organic or inorganic acids (such as saturated aliphatic carboxylic acids containing 1 to 4 carbon atoms, the hydrocarbon chain of which is optionally substituted by one or more halogen atoms such as chlorine or bromine, or by a phenyl radical; benzoic acid; hydrazoic acid; thiocyanic acid; hydrochloric acid or hydrofluoric acid) and alkali metal or alkaline earth metal salts of weakly acidic compounds (such as thiophenol, 2-mercaptobenzothiazole, 2-mercapto-5-methyl-1,3,4-thiadiazole, 5-mercapto-1-methyl-tetrazole or phthalimide). Dimethylformamide, dimethylsulphoxide, hexamethylphosphotriamide or N-methylpyrrolidone are preferred as the polar solvent. The amount of the weak base is not critical and can vary from merely catalytic amounts to one equivalent per mol of the compound of formula (IV); 1/20 to 1/10 equivalent per mole of the compound of formula (IV) is generally used.

Preferred compounds of formula (IV) are those in which $R_2$ represents a 2-benzothiazolyl, 5-methyl-2-thiadiazolyl or 5-tetrazolyl group.

When $R_3$ is a benzyl or phenoxymethyl group, the substitution of the $R_3CO-$ group by a trichloroacetyl group is performed using the conditions described above for converting a compound of formula (III) to one of formula (I).

The compounds of the general formula (II) can be prepared in accordance with the following processes, which are described and claimed in our copending application Ser. No. 503,278 filed Sept. 5, 1974.

1. Oxidation of the sulphur atom of a compound of the formula:

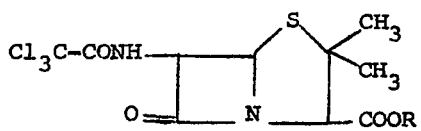

wherein R is as defined above.

This oxidation can be effected by any method for oxidising a 6-amino-penicillanic acid to the corresponding sulphoxide. Hydrogen peroxide, an organic per-acid such as p-nitroperbenzoic acid or sodium periodate are examples of suitable oxidising agents.

2. Replacement of the $R_1CO-$ group of a compound of the formula:

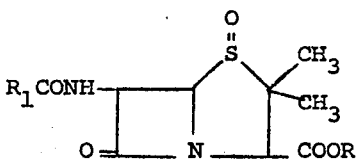

wherein R and $R_1$ are as defined above, by a trichloroacetyl group.

The compounds of formula (V) can be prepared by replacing the $R_1CO-$ group of a compound of the general formula:

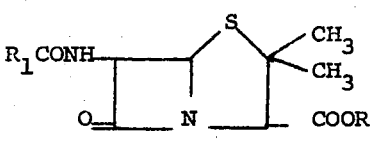

wherein R and $R_1$ are as defined above, by a trichloroacetyl group. This replacement can be carried out using the conditions described above for converting a compound of formula (III) to one of formula (I).

The compounds of formula (VII) can be prepared by esterifying a compound of formula

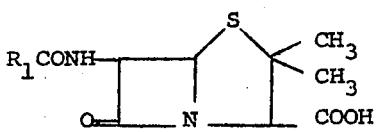

wherein $R_1$ is a benzyl radical (penicillin G) or a phenoxymethyl radical (penicillin V).

This esterification can be carried out by any conventional esterification method which does not affect the rest of the molecule.

The compounds of formula (VI) can be prepared:
a. By oxidation of a compound of formula (VII).

The conditions generally used are those described above for oxidising a compound of formula (V) to one of formula (II).

b. By esterification of a compound of the formula:

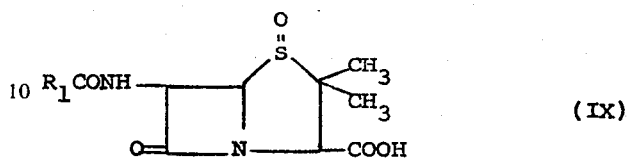

wherein $R_1$ is as defined above. As mentioned above any esterification method which does not affect the rest of the molecule can be used.

The compounds of the formula (IX) can be prepared by oxidation of a compound of the formula (VIII). The conditions generally used are those described above for oxidising a compound of the formula (V) to one of formula (II).

The compounds of formula (IV) can be prepared by reacting a thiol of formula:

$$R_2SH \quad (X)$$

wherein $R_2$ is as defined above, with a compound of the formula:

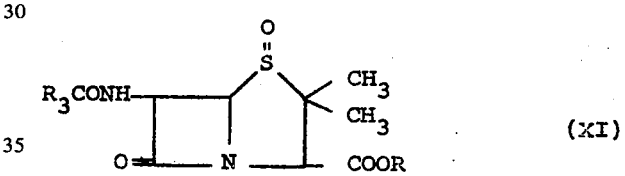

wherein R and $R_3$ are defined as above, using the conditions described in an article by T. Kamiya et al., *Tetrahedron Letters*, 1973 32, 3001.

2-Mercapto-benzothiazole, 2-mercapto-5-methyl-1,3,4-thiadiazole or 5-mercapto-1-methyl-tetrazole are preferably used, using as solvent an inert organic solvent such as toluene, the reaction being performed at the reflux temperature of the reaction medium.

The compounds of formula (I) are useful for the preparation of 7-amino-3-desacetoxy-cephalosporanic acid (7-ADCA) of the formula:

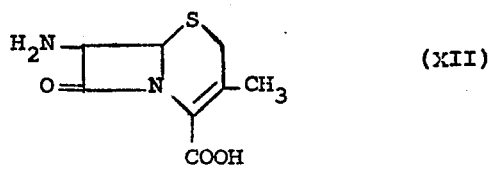

which is used as a starting material for the preparation of cephalexin and other semi-synthetic cephalosporin derivatives which exhibit noteworthy antibiotic acitivity.

The invention therefore also provides a process for the preparation of 7-ADCA which comprises replacing the trichloroacetyl and R groups of a compound of formula (I) by hydrogen atoms.

Depending on the meaning of R, the substitution of the trichloroacetyl and R groups can be carried out by replacing the R group first, followed by the trichloroacetyl group, or vice versa.

When R is a 2,2,2-trichloroethyl group, initial reaction with zinc in acetic acid converts the R-group into a hydrogen atom and the trichloroacetyl group into a monochloroacetyl group to give a compound of the formula:

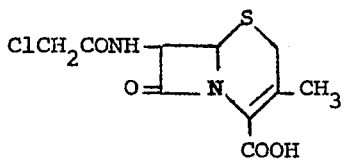

which is then treated with thriourea in an aqueous medium in accordance with the method of J. D. Cocker et al., J. Chem. Soc., 1965, 5015, to replace the monochloroacetyl group with a hydrogen atom.

When R is other than a 2,2,2-trichloroethyl radical, it is first replaced by a hydrogen atom using any conventional method for conversion of an ester to an acid without affecting the rest of the molecule. For example by hydrolysis in an acid medium, preferably in the presence of trifluoroacetic acid, hydrogenolysis, or the action of an alkali metal thiophenolate. A compound of the formula:

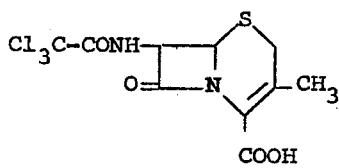

is obtained, the trichloroacetyl radical then being replaced by a hydrogen atom by treating this compound with an alkali metal borohydride such as sodium or potassium borohydride, in an ethanolic medium (see F. Weygand, Chem. Ber., 1970, 103, 2437).

When R is other than a 2,2,2-trichloroethyl or phenacyl radical, the trichloroacetyl radical is replaced by a hydrogen atom first, by effecting a treatment employing an alkali metal borohydride such as sodium or potassium borohydride, in an ethanolic medium, to give a product of the formula:

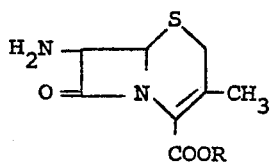

the R group then being replaced by a hydrogen atom using any conventional method for converting an ester into an acid without affecting the rest of the molecule, such as those described above.

The present invention thus provides 7-amino-3-desacetoxy-cephalosporanic acid when prepared from compounds of formula (I).

The present invention makes it possible to prepare 7-ADCA from an inexpensive and readily available penicillin such as penicillin G. The phenylacetyl group of penicillin G can be replaced directly and easily by a trichloroacetyl group and, after oxidation of the sulphur atom, rearrangement of the resultant sulphoxide of formula (II) yields the cephalosporin derivative of the formula (I). Replacement of the trichloroacetyl and R groups of the compounds of Formula (I) by hydrogen atoms can be performed using mild conditions, good yields being obtained.

The following Examples illustrate the invention. The main infra-red absorption bands of the products are characterized by their wave numbers (in $cm^{-1}$). N.M.R. shifts are in p.p.m.

EXAMPLE 1

A solution of trichloroethyl 6β-trichloroacetamido-penicillanate 1β-oxide (5.09 g) and methanesulphonic acid (1.21 g) in a mixture of benzene (330 cc.) and dimethylacetamide (60 cc.) is heated under reflux for 18 hours, the water formed during the reaction being removed as it is formed by passing the condensate over calcium chloride before reintroducing it into the reaction medium.

The brown-coloured reaction mixture is diluted with benzene (400 cc.) and is poured into distilled water (1 liter) containing sodium bicarbonate (2 g). After decanting, the organic phase is washed with water (3 times 400 cc.), dried over sodium sulphate and concentrated under reduced pressure (12 mm Hg) at 40°C to a volume of 10 cc. The solution thus obtained is chromatographed on a column of silica gel (75 g) (0.05–0.20 mm, pH neutral; diameter of the column: 2cm, height: 39 cm). Elution is carried out using benzene, collecting 50 cc fractions. Fractions 37 to 150 are combined and are evaporated under reduced pressure (12 mm Hg) at 30°C to give 3-methyl-8-oxo-7-trichloroacetylamino-2-trichloroethoxycarbonyl-5-thia-1-aza-bicyclo[4,2,0]oct-2-ene (2.33 g) in the form of a light maroon solid.

The starting trichloroethyl 6β-trichloroacetamido-penicillinate 1β-oxide can be prepared in accordance with one of the following methods:

a. Trichloroacetyl chloride (16.6 cc.) is added dropwise, over the course of 30 minutes and with vigorous stirring, to a solution, cooled to −10°C, of trichloroethyl 6β-phenylacetamido-penicillanate 1β-oxide (31.2 g) in anhydrous pyridine (180 cc.). The mixture is then stirred for 1 hour 30 minutes, the temperature rising from −7°C at the end of the addition to −2°C. The brown mixture is then poured into water (500 cc.) to which crushed ice has been added. A maroon paste-like product settles out; after removing the liquid phase by decanting, this product is triturated in water (200 cc.) and is then taken up in ethyl acetate (1 liter). The organic phase is washed with water (3 times 500 cc.), dried over sodium sulphate, filtered and concentrated to dryness under reduced pressure (12 mm Hg) at 30°C. The solid obtained is dissolved in benzene (200 cc.) and the solution obtained is chromatographed on a column of silica gel (500 g) (0.05–0.2 mm, pH neutral; diameter of the column: 6 cm, height: 45 cm).

Elution is carried out successively with benzene (2 liters), a mixture of benzene and ethyl acetate (99.5/0.5 by volume) (2 liters), a mixture of benzene and ethyl acetate (99/1 by volume) (6 liters) and then a mixture of benzene and ethyl acetate (98/2 by volume) (10 liters), collecting 500 cc. fractions. Fractions 19 to 32 are combined and concentrated to dryness under reduced pressure (12 mm Hg) at 40°C. 2,2,2-Trichloroethyl 6β-trichloroacetamido-penicillanate 1β- oxide (14 g) is obtained in the form of a light yellow solid.

Trichloroethyl 6β-phenylacetamido-penicillanate 1β-oxide can itself be prepared in the following way:

A solution of 98% pure p-nitroperbenzoic acid (24.2 g) in chloroform (1.5 liters) is added dropwise, with stirring and over the course of 2 hours, to a solution, cooled to −5°C, of the trichloroethyl ester of penicillin G (55.9 g) in chloroform (600 cc.), the temperature being kept below 0°C. Thereafter, the mixture is stirred for 2 hours at 0°C and then the p-nitrobenzoic acid which has precipitated is filtered off. The filtrate is washed successively with a chilled saturated solution of sodium bicarbonate (3 times 300 cc.) and chilled water (twice 300 cc.), and is then dried over sodium sulphate. After filtration and concentration to dryness under reduced pressure (12 mm Hg) at 30°C, the residue is taken up in diethyl ether (300 cc.). After filtration and drying, trichloroethyl 6β-phenylacetamido-penicillanate 1β-oxide (53.35 g) is obtained, the characteristics of which are as follows:

NMR spectrum (CDCl$_3$): 1.28 (S, 3H) —CH$_3$; 1.75 (S, 3H) —CH$_3$; 3.55 (S, 2H) —CH$_2$CO—; 4.6 and 4.85 (DD, AB, J = 12, 2H) —COOCH$_2$CCl$_3$; 4.65 (S, 1H) —H in the 3-position; 4.9 (D, J = 4.5, 1H) —H in the 5-position; 5.95 (DD, J = 10 and 4.5, 1H), —H in the 6-position, 7 (D, J = 10, 1H) —NH—; and 7.2 (S,5H) C$_6$H$_5$—.

Infra-red spectrum (determination using a solution in bromoform) 3395, 1680 and 1503: amide; 1800: carbonyl of the β-lactam; 1775, 1275 and 820: ester; 1035: sulphoxide; 1390 and 1370: gem-dimethyl; and 770 and 715: phenyl.

b. A solution of 98% p-nitroperbenzoic acid (2.02 g) in chloroform (150 cc.) is added dropwise, with stirring, to a solution, cooled to −2°C, of trichloroethyl trichloroacetamido-penicillanate (4.9 g) in chloroform (50 cc.). Thereafter, the mixture is stirred for 2 hours at 0°C and then the p-nitrobenzoic acid which has precipitated is filtered off. The filtrate is washed with a 5% strength solution of sodium bicarbonate (twice 100 cc.) and water (twice 100 cc.) and then dried over sodium sulphate. After filtration and concentration to dryness under reduced pressure (12 mm Hg) at 30°C, the residue is taken up in diethyl ether (100 cc.), filtred and dried to give trichloroethyl 6β-trichloroacetamido-penicillanate 1β-oxide (2.6 g), Rf = 0.59 [silica gel; chloroform/ethyl acetate (80/20 by volume)]

Optical rotation: $[\alpha]_D^{20} = +143°$ (c = 0.908; chloroform)

Analysis: Calculated %: C 28.32, H 2.38, N 5.50, S 6.30, Cl 41.79. Found: 28.8, 2.45, 5.3, 5.8, 41.1.

NMR spectrum (CDCl$_3$): 1.36 (S, 3H) — CH$_3$; 1.85 (S, 3H) —CH$_3$; 4.7 and 5.05 (AB, J = 13, 2H) —COOCH$_2$CCl$_3$; 4.85 (S, 1H) —H in the 3-position; 5.15 (D, J = 4.5, 1H) —H in the 5-position; 5.95 (DD, J = 4.5 and 10, 1H) —H in the 6-position; and 8.45 (D, J = 10, 1H) —NH—.

Infra-red spectrum (determination using a solution in bromoform): 3350, 1715 and 1505: amide: 1800: carbonyl of the β-lactam; 1762, 1275 and 815: ester; 1035: sulphoxide; and 1390 and 1370: gem-dimethyl.

Trichloroethyl trichloroacetamido-penicillanate can be prepared by one of the following methods:

a. Trichloroacetyl chloride (2.48 cc.) is added dropwise, over the course of 4 minutes and with vigorous stirring, to a solution, cooled to −10°C, of the trichloroethyl ester of penicillin G (4.65 g) in pyridine (26 cc.). Thereafter, the mixture is stirred for 1 hour at a temperature of between −4° and −2°C. The reaction mixture is then poured into chilled water (50 cc.) and the paste-like product which settles out is then taken up in ethyl acetate (50 cc.). The organic phase is washed with water (3 times 25 cc.) and then dried over sodium sulphate. After filtration and concentration to dryness under reduced pressure (12 mm Hg) at 30°C, the residue obtained is dissolved in benzene (20 cc.) and chromotographed on a column of silica gel (75 g) (0.05–0.20 mm, pH neutral; diameter of the column: 2.4 cm, height: 14 cm). Elution is carried out with benzene (6 liters), collecting 50 cc. fractions. Fractions 25 to 75 are combined and concentrated to dryness under reduced pressure (12 mm Hg) at 30°C. Trichloroethyl trichloroacetamido-penicillanate (0.85 g) is obtained.

b. Anhydrous pyridine (27 cc.) is added to a solution, kept at −10°C, of the trichloroethyl ester of penicillin G (54.6 g) in toluene (1,300 cc.), and then a solution of phosphorus pentachloride (18.3 g) in anhydrous toluene (330 cc.) is added dropwise over the course of 40 minutes, at a temperature of between −5° and −2°C. The reaction mixture is stirred for 1 hour at a temperature of about −2°C and is then poured into chilled water (500 cc.), with stirring. After decanting, the organic phase is washed successively and rapidly with a chilled saturated solution of sodium chloride (250 cc.), then with a 5% strength chilled solution of sodium bicarbonate (250 cc.) and with a chilled saturated solution of sodium chloride (250 cc.). After drying at 0°C over magnesium sulphate and filtration, a solution of potassium trichloroacetate (20 g) in acetonitrile (1 liter) is added to the filtrate and the mixture is stirred for 16 hours at a temperature of about 20°C. The brown mixture obtained is concentrated by dryness under reduced pressure (12 mm Hg) at 30°C and the residue is taken up in chloroform (200 cc.). The solution is filtered and chomatographed on a column of silica gel (500 g) (0.05–0.20 mm, pH neutral; diameter of the column: 5.5 cm, height: 50 cm). Elution is carried out with chloroform (10 liters), collecting 250 cc. fractions. Fractions 7 to 14 are combined and evaporated under reduced pressure (12 mm Hg) at 30°C to give trichloroethyl trichloroacetamido-penicillanate (6g) in the form of a light yellow solid, the characteristics of which are as follows: Rf = 0.85 [silica gel; chloroform/ethyl acetate (80/20 by volume)]

Infra-red spectrum (determination using a solution in bromoform) 3395, 1715 and 1505: amide, 1782: carbonyl of the β-lactam; 1760, 1230 and 810: ester; and 1395 and 1367: gem-dimethyl.

EXAMPLE 2

Trichloroacetyl chloride (1.04 cc.) is added, over the course of 30 minutes and with vigorous stirring, to a solution, cooled to −10°C, of 3-methyl-8-oxo-7-phenylacetamido-2-trichloroethoxycarbonyl-5-thia-1-aza-bicyclo[4,2,0]oct-2-ene (1.38 g) in pyridine (15 cc.). Thereafter, the mixture is stirred for 2 hours 30 minutes at a temperature of between −3° and −1°C. The mixture is then poured into water and crushed ice (100 cc.) and a maroon paste-like product settles out. After removing the liquid phase by decanting, this product is triturated in water (50 cc.) and is then taken up in ethyl acetate (200 cc.). The organic phase is washed with water (3 times 200 cc.), dried over sodium sulphate, filtered and concentrated to dryness under reduced pressure (12 mm Hg) at 30°C. The solid obtained is dissolved in benzene (20 cc.) and the solution obtained is chromatographed on a column of silica gel (20 g) (0.05–0.20 mm, pH neutral; diameter of the column: 1.5 cm, height: 20 cm). Elution is carried out successively with benzene (300 cc.), a mixture of benzene and ethyl acetate (99.5/0.5 by volume) (300 cc.) and a mixture of benzene and ethyl acetate (99/1 by volume) (600 cc.), collecting 25 cc. fractions. Fractions 6 to 36 are combined and concentrated to dryness under reduced pressure (12 mm Hg) at 30°C. 3-methyl-8-oxo-7-trichloroacetamido-2-trichloroethoxycarbonyl-5-thia-1-aza-bicyclo[4,2,0]oct-2-ene (450 mg) is obtained in the form of a light maroon solid, the characteristics of which are as Follows:RF = 0.63 [silica gel; chloroform/ethyl acetate (80/20 by volume)]

Optical rotation: $[\alpha]_D^{20} = +71°$ (c = 0.5; chloroform)
Analysis: Calculated %: C 29.35, H 2.05, N 5.71, S 6.53, Cl 43.32. Found: 29.4, 2.2, 5.65, 6.45, 43.3.

NMR spectrum (CDCl$_3$): 2.25 (S, 3H) —CH$_3$; 3.35 and 3.55 (AB, J = 18, 2H) —SCH$_2$—; 4.80 and 4.95 (AB, J = 14, 2H) —COOCH$_2$CCl$_3$; 5.12 (D, J = 5, 1H) —H in the 6-position; 5.70 (DD, J = 5 and 8, 1H) —H in the 7-position; and 7.75 (D, J = 8, 1H) —NH—.

Infra-red spectrum (determination using a solution in bromoform): 3400, 1720 and 1510: amide; 1782: carbonyl of the β-lactam; 1725, 1212 and 820: ester; and 1635: ethylenic double bond.

EXAMPLE 3

A solution of p-methoxybenzyl 6β-trichloroacetamido-penicillanate 1β-oxide (4.97 g), pyridine (0.16 cc.) and 85% pure orthophosphoric acid (0.136 cc.) in a mixture of deperoxidised dioxane (400 cc.) and benzene (200cc.) is heated under reflux for 20 hours, the water formed during the reaction being removed as it is formed by passing the condensate over a molecular sieve before reintroducing it into the reaction medium.

The brown-coloured reaction mixture is diluted with benzene (400 cc.) and poured into chilled distilled water (1 liter). The mixture is decanted and then the organic phase is washed with distilled water (4 times 200 cc.). After drying and filtration, it is concentrated to dryness under reduced pressure (12 mm Hg) at 30°C. The residue is taken up in benzene (20 cc.) and the black solution obtained is chromatographed on a column of silica gel (50 g) (0.05–0.20 mm, pH neutral; diameter of the column: 2 cm, height: 30 cm). Elution is carried out successively with benzene (500 cc.), a mixture of benzene and ethyl acetate (99.5/0.5 by volume) (1 liter) and a mixture of benzene and ethyl acetate (99/1 by volume) (1 liter), collecting 50 cc. fractions. Fractions 24 to 50 are combined and concentrated to dryness under reduced pressure (12 mm Hg) at 30°C. 2-p-Methoxybenzyloxycarbonyl-3-methyl-8-oxo-7-trichloroacetamido-5-thia-1-aza-bicyclo-[4,2,0]oct-2-ene (1.7 g) is thus obtained, the characteristics of which are as follows: Rf = 0.59 [silica gel; chloroform/ethyl acetate (80/20 by volume)]

Analysis: calculated %: C 45.06, H 3.57, N 5.84, S 6.68, Cl 22.17. Found: 45.4, 3.70, 6.10, 6.65, 22.3.

Optical rotation: $[\alpha]_D^{20} = +54.8°$ (c = 0.92; chloroform)

NMR spectrum (CDCl$_3$): 2.16 (S, 3H) —CH$_3$; 3.25 and 3.40 (AB, J = 9.5, 2H) —SCH$_2$—; 3.80 (S, 3H) —OCH$_3$; 4.98 (D, J = 5, 1H) —H in the 6-position; 5.18 (S, 2H) —COOCH$_2$—; 5.60 (DD, J = 5 and 9, 1H) —H in the 7-position; 6.86 and 7.30 (AA'BB', 4H) —C$_6$H$_4$—; and 7.62 (D, J = 9, 1H) —NH—.

Infra-red spectrum (determination using a solution in bromoform: 3405, 1720 and 1515: amide; 2840, 1240, 1030 and 820: p-methoxyphenyl; 1780: carbonyl of the β-lactam; 1720 and 1220: ester; 1635: ethylenic double bond; 1360: methyl; and 820: trichloromethyl.

The starting p-methoxybenzyl 6β-trichloroacetamido-penicillanate 1β-oxide can be prepared in the following way:

Trichloroacetyl chloride (22 cc.) is added dropwise, over the course of 30 minutes and with vigorous stirring, to a solution, cooled to −10°C, of p-methoxybenzyl 6β-phenylacetamido-penicillanate 1β-oxide (42 g) in anhydrous pyridine (250 cc.). Thereafter, the mixture is stirred for 1 hour 30 minutes at a temperature of between −4° and −2°C. The brown reaction mixture is poured into water (500 cc.) to which crushed ice has been added. A maroon paste-like product settles out; after removing the liquid phase by decanting, this product is triturated in water (200 cc.) and is taken up in ethyl acetate (1 liter). The organic phase is washed with water (3 times 500 cc.), dried over sodium sulphate, filtered and concentrated to dryness under reduced pressure (12 mm Hg) at 30°C. The solid obtained is dissolved in benzene (100 cc.) and the solution obtained is chromatographed on a column of silica gel (500 g) (0.05–0.20 mm, pH neutral; diameter of the column: 6 cm, height: 43 cm). Elution is carried out successively with benzene (1 liter), a mixture of benzene and ethyl acetate (99/1 by volume) (6 liters), a mixture of benzene and ethyl acetate (98/2 by volume) (10 liters) and a mixture of benzene and ethyl acetate (97/3 by volume) (10 liters), collecting 300 cc. fractions. Fractions 34 to 56 are combined and concentrated to dryness under reduced pressure (12 mm Hg) at 30°C. β-Methoxybenzyl 6β-trichloroacetamido-penicillanate 1β-oxide (12.5 g) is obtained in the form of a light yellow solid, the characteristics of which are as follows:Rf = 0.50 [silica gel; chloroform/ethyl acetate (80/20 by volume)]

Analysis: Calculated %: C 43.43, H 3.85, N 5.63, S 6.44, Cl 21.37. Found: 43.6, 3.80, 6.0, 6.35, 21.5.

Optical rotation:$[\alpha]_D^{20} = +162°$ (c = 1.04; chloroform)

NMR spectrum (CDCl$_3$): 1.10 (S, 3H) —CH$_3$; 1.70 (S, 3H) —CH$_3$; 3.80 (S, 3H) —OCH$_3$; 4.68 (S, 1H) —H in the 3-position; 5.12 (D, J = 4.5, 1H) —H in the 5-position; 5.10 and 5.25 (AB, J = 12, 2H) —COOCH$_2$—; 5.88 (DD, J = 10 and 4.5, 1H) —H in the 6-position; 6.90 and 7.30 (AB, J = 9, 4H) —C$_6$H$_4$—; and 8.50 (D, J = 10, 1H) —NH—.

Infra-red spectrum (determination using a solution in bromoform): 3350, 1720 and 1515: amide; 2838, 1245, 1030 and 820: p-methoxyphenyl; 1800: carbonyl of the β-lactam; 1745 and 1200: ester; 1390 and 1368: gem-dimethyl; 1030: sulphoxide; and 820: trichloromethyl. p-Methoxybenzyl 6β-phenylacetamido-penicillanate 1β-oxide can be prepared by following the procedure described in Example 1 for the preparation of trichloroethyl 6β-phenylacetamido-penicillanate 1β-oxide, but starting from the p-methoxybenzyl ester of penicillin G (69 g) in chloroform (750 cc.) and p-nitroperbenzoic acid (30 g) in chloroform (2 liters). After crystallisation from chloroform (100 cc.) to which ether (300 cc.) has been added, p-methoxybenzyl 6β-phenylacetamido-penicillanate 1β-oxide (51 g) is obtained in the form of a white solid, the characteristics of which are as follows:

NMR spectrum (CDCl$_3$): 1.05 (S, 3H) —CH$_3$; 1.65 (S, 3H) —CH$_3$; 3.56 (S, 2H) —CH$_2$CO—; 3.80 (S, 3H) —OCH$_3$; 4.60 (S, 1H) —H in the 3-position, 4.93 (D, J = 5, 1H) —H in the 5-position; 5.06 and 5.22 (AB, J = 12, 2H) —COOCH$_2$—; 5.98 (DD, J = 5 and 10, 1H) —H in the 6-position; 7.1 (D, J =10, 1H) —NH—; 6.9 and 7.30 (AB, J = 9, 4H) —C$_6$H$_4$—; and 7.32 (S, 5H) C$_6$H$_5$—.

Infra-red spectrum (determination using a solution in bromoform): 3395, 1680 and 1510: amide; 1798: carbonyl of the β-lactam; 1745 and 1200: ester; 2838, 1245, 1030 and 820: p-methoxyphenyl; 1030: sulphoxide; and 1390 and 1368: gem dimethyl.

EXAMPLE 4

A mixture of 4-(2-benzothiazolyl-dithio)-3-trichloroacetamido-1-(1-trichloroethoxycarbonyl-2-methyl-prop-2-en-1-yl)-2-azetidinone (2 g) and sodium acetate (25 mg) in dimethylsulphoxide (20 cc.) to which dimethylformamide (4 cc.) has been added is stirred under a nitrogen atmosphere at +5°C for 2 hours 30 minutes. The reaction mixture is poured into water which is saturated with sodium chloride and to which crushed ice has been added (200 cc.), and the resulting mixture is extracted with benzene (100 cc. followed by 3 times 50 cc.). The benzene extracts are combined and washed with distilled water (3 times 100 cc.), dried over sodium sulphate, filtered and concentrated to dryness under reduced pressure (12 mm Hg) at 30°C. The residue obtained is dissolved in methylene chloride (25 cc.) and the solution obtained is chromatographed on a column containing silica (30 g) (0.06–0.20 mm; pH neutral; diameter of the column: 1.7 cm, height: 20 cm). Elution is carried out using methylene chloride and collecting 50 cc. fractions. Fractions 5 to 8 are combined and concentrated under reduced pressure (12 mm Hg) at 30°C. On being treated with diethyl ether (5 cc.) the residue crystallises. After filtration and drying, 3-methyl-8-oxo-7-trichloroacetamido-2-trichloroethoxycarbonyl-5-thia-1-axa-bicyclo[4,2,0]oct-2-ene (0.55 g) is obtained in the form of a light maroon solid, the chracteristics of which are identical to those of the product of Example 2. 4-(2-Benzothiazolyl-dithio)-3-trichloroacetamido-1-(3-trichloroethoxycarbonyl-2-methyl-prop-2-en-1-yl)-2-azetidinone used as the starting product can be prepared in the following way:

A solution of trichloroethyl 6β-trichloroacetamido-penicillanate 1β-oxide (3.56 g) and 2-mercapto-benzothiazole(1.17 g) in toluene (150 cc.) is heated under reflux for 1 hour 15 minutes, and the water formed during the reaction is removed as it is formed by passing the condensate over calcium chloride before reintroducing it into the reaction mixture. The solvent is evaporated under reduced pressure (12 mm Hg) at 40°C; the residue is taken up in chloroform (10 cc.) and the solution obtained is chromatographed on a column containing silica (100 g) (0.06–0.20 mm; pH neutral; diameter of the column: 2.4 cm, height: 46 cm). Elution is carried out using chloroform, collecting 50 cc. fractions. Fractions 3 to 7 are combined and concentrated under reduced pressure (12 mm Hg) at 30°C. 4-(2-Benzothiazolyl-dithio)-3trichloroacetamido-1-(1-trichloroethoxycarbonyl-2-methyl-prop-2-en-1-yl)-2-azetidinone (3.02 g) is obtained in the form of a light maroon solid, the characteristics of which are as Follows:RF = 0.60 [silica gel; chloroform/ethyl acetate (85/15 by volume]

Optical rotation: $[\alpha]_D^{20} = -88°$ (c = 1.02, chloroform)

NMR spectrum (CDCl$_3$): 2.1 (S, 3H) —CH$_3$; 4.8 (AB, J = 12, 2H) —COOCH$_2$CCl$_3$; 5.18 (S, 1H) —CHCOO—; 5.25 (S wide, 1H) and 5.30 (S wide, 1H) = CH$_2$; 5.40 (DD, J = 8 and 4, 1H) —H in the 3-position; 5.60 (D, J = 4, 1H) —H in the 4-position; 5.65 (D, J = 8, 1H) —CONH—; and 7 to 8.1 (hump, 4H) aromatic protons.

Infra-red spectrum: (determination using a solution in bromoform) 3400, 1720 and 1510: amide; 1780: carbonyl of the β-lactam; 1755: ester; and 820: trichloromethyl.

EXAMPLE 5

A mixture of 4-(2-benzothiazolyl-dithio)-3-phenylacetamido-1-(1-trichloroethoxycarbonyl-2-methyl-prop-2-en-1-yl)-2-azetidinone (6.30 g) and anhydrous sodium acetate (0.82 g) in anhydrous dimethylformamide (60 cc.) is stirred under a nitrogen atmosphere at a temperature of −35°to −28°C for 4 hours 15 minutes. The brown reaction mixture is poured into water which is saturated with sodium chloride and to which crushed ice has been added (300 cc) and then the resulting mixture is extracted with benzene (200 cc.). The organic phase is washed with distilled water (5 times 100 cc.), dried over sodium sulphate, filtered and concentrated to dryness under reduce pressure (12 mm Hg) at 25°C. The product obtained is dissolved in methylene chloride (50 cc.) and the solution obtained is chromatographed on a column of silica (100 g) (0.06–0.02 mm; pH neutral; diameter of the column: 2.5 cm, height: 25 cm). Elution is carried out using methylene chloride, collecting 50 cc. fractions. Fractions 9 to 16 are combined and concentrated to dryness under reduced pressure (12 mm Hg) at 25°C. 3-Methyl-8-oxo-7-phenylacetamido-2-trichloroethoxycarbonyl-5-thia-1-aza-bicyclo[4,2,0]oct-2-ene (1.95 g) is obtained; it melts at 162°C and its chracteristics are as follows:

Elementary analysis: Calculated %: C 46.63, H 3.69, N 6.04, S 6.91, Cl 22.93, O 12.8. Found: 47.2, 3.7, 5.8, 7.0, 23.15, 14.1.

Optical rotation: $[\alpha]_D^{20} = +50°$ (c = 1.07, chloroform)

NMR spectrum (CDCl$_3$): 2.20 (S, 3H) —CH$_3$; 3.40 (AB, J = 19, 2H) —SCH$_2$—; 3.65 (S, 2H) —CH$_2$CO—; 4.95 (AB, J = 12.5, 2H) —CH$_2$CCl$_3$; 5.0 (D, J = 5, 1H) —H in the 6-position; 5.82 (DD, J = 9 and 5, 1H) —H in the 7-position; 6.60 (D, J= 9, 1H) —NH—; and 7.37 (S, 5H) C$_6$H$_5$—.

Infra-red spectrum (determination using a solution in bromoform): 3410, 1680 and 1505: amide; 1780: carbonyl of the β-lactam; 1753: ester; and 820: trichloromethyl. Trichloroacetyl chloride (1.23 cc.) is added over the course of 2 minutes, and with vigorous stirring, to a solution, cooled to −11°C, of 3-methyl-8-oxo-7-phenylacetamido-2-trichloroethoxycarbonyl-5-thia-1-aza-bicyclo[4,2,0]oct-2-ene (4.63 g) in pyridine (50 cc.), and then the temperature of the mixture is kept thereafter between −6°C and −3°C for 2 hours. The reaction mixture is poured into a mixture of water and ice (100 cc.); a maroon paste-like product settles out; the supernatant liquid is removed by decanting and the product is taken up in ethyl acetate (220 cc.). The organic phase is washed with water (3 times 100 cc.), dried over sodium sulphate, filtered and concentrated to dryness under reduced pressure (12 mm Hg) at 30°C. The solid obtained is dissolved in benzene (30 cc.) and the solution obtained is chromatographed on a column containing silica (70 g) (0.06–0.20 mm; pH neutral; diameter of the column: 2.4 cm, height: 34 cm). Elution is carried out successively with benzene (500 cc.), a mixture of benzene and ethyl acetate (99.5/0.5 by volume) (500 cc.) a mixture of benzene and ethyl acetate (99/1 by volume) (500cc.), a mixture of benzene and ethyl acetate (98/2 by volume) (1.5 liters), a mixture of benzene and ethyl acetate (96/4 by volume) (1 liters) and a mixture of benzene and ethyl acetate (92/8 by volume) (1.25 liters), collecting 60 cc. fractions. Fractions 18 to 45 are combined and concentrated to dryness under reduced pressure (12 mm Hg) at 30°C. 3-Methyl-8-oxo-7-trichloroacetamido-2-trichloroethoxycarbonyl-5-thia-1-aza-bicyclo-(4,2,0]oct-2-ene (1.65 g), the characteristics of which are identical to those of the product of Example 4, is thus obtained. 4-(2-Benzothiazolyl-dithio)-3-phenylacetamido-1-(1-trichloroethoxycarbonyl-2-methyl-prop-2-en-1-yl)-2-azetidinone used as the starting product can be prepared in the following way:

A solution of trichloroethyl 6β-phenylacetamidopenicillanate 1β-oxide (120.4 g) and 2-mercaptobenzothiazole (41.8 g) in toluene (2,500 cc.) is heated under reflux for 4 hours. The water formed during the reaction is removed as it is formed by passing the condensate over calcium chloride before reintroducing it into the reaction mixture. The solvent is evaporated under reduced pressure (12 mm Hg) at 50°C and then the yellow paste-like residue is taken up in boiling carbon tetrachloride (500 cc.). The solution is cooled to a temperature of about 3°C; the crystals which appear are filtered off and then dried under reduced pressure. 4-(2-Benzothiazolyl-dithio)-3-phenylacetamido-1-(1-trichloroethoxycarbonyl-2-methyl-prop-2-en-1-yl)-2-azetidinone (142 g) is thus obtained in the form of a white crystalline solid which melts at 133°–134°C and the characteristics of which are as follows; Rf = 0.70 [silica gel; chloroform/ethyl acetate (50/50 by volume)]

Optical rotation: $[\alpha]_D^{20} = -80.6°$ (c = 0.996, chloroform)

NMR spectrum (CDCl$_3$): 2.02 (S, 3H) —CH$_3$; 3.75 (S, 2H) —CH$_2$CO—; 4.78 (AB, J = 11, 2H) —COOCHCCl$_3$; 5.1 (S, 1H) —CHCOO—; 5.2 (S wide, 1H) and 5.3 (S wide, 1H) =CH$_2$; 5.4 (DD, J = 8 and 4.5, 1H) —H in the 3-position; 5.55 (D, J = 4.5, 1H) —H in the 4-position; 6.55 (D, J = 8, 1H) —CONH—; and 7.4 to 8 (hump, 9H) aromatic protons.

Infra-red spectrum (determination using a solution in bromoform):3415, 1680 and 1505: amide; 1770: carbonyl of the β-lactam; and 1760: ester.

EXAMPLE 6

A mixture of 4-(2-benzothiazolyl-dithio)-3-phenylacetamido-1-(1-trichloroethoxycarbonyl-2-methyl-prop-2-en-1-yl)-2-azetidinone (6.30 g) and anhydrous sodium acetate (0.080 g) in dimethylsulphoxide (60 cc.) is stirred under a nitrogen atmosphere at a temperature of +5°C for 2 hours 45 minutes. The brown reaction mixture is poured into water which is saturated with sodium chloride and to which crushed ice has been added (300 cc.) and then the resulting mixture is extracted with benzene (250 cc. followed by 3 times 100 cc.). The benzene extracts are combined and washed with water (5 times 100 cc.), dried over sodium sulphate, filtered and concentrated to dryness under reduced pressure (12 mm Hg) at 30°C. The solid brown residue is taken up in diethyl ether (100 cc.) with which it is left in contact for 12 hours at a temperature of about 20°C. After filtration and drying, 3-methyl-8-oxo-7-phenylacetamido-2-trichloroethoxycarbonyl-5-thia-1-aza-bicyclo[4,2,0]-oct-2-ene (1.60 g) is obtained in the form of a pale pink crystalline solid which melts at 161°–162°C.

EXAMPLE 7

A mixture of 4-(2-benzothiazolyl-dithio)-3-phenylacetamido-1-(1-trichloroethoxycarbonyl-2-methyl-prop-2-en-1-yl)-2-azetidinone (6.30 g) and sodium nitride (0.065 g) in anhydrous dimethylsulphoxide (60 cc.) is stirred under a nitrogen atmosphere at a temperature of 20°C for 2 hours. The reaction mixture is poured into water which is saturated with sodium chloride and to which crushed ice has been added (500 cc.), and then the resulting mixture is extracted with benzene (250 cc. followed by 3 times 100 cc.). The benzene extracts are washed with water (5 times 100 cc.), dried over sodium sulphate, filtered and concentrated to dryness under reduced pressure (12 mm Hg) at 30°C. The solid residue is taken up in diethyl ether (100 cc.) with which it is left in contact for 2 hours at a temperature of about 20°C. After filtration and drying, 3-methyl-8-oxo-7-phenylacetamido-2-trichloroethoxycarbonyl-5-thia-1-aza-bicyclo[4,2,0]oct-2-ene (2.30 g) is obtained in the form of a white crystalline solid which melts at 162°C.

EXAMPLE 8

A mixture of 4-(5-methyl-2-thiadiazolyldithio)-3-phenylacetamido-1-(1-trichloroethoxycarbonyl-2-methyl-prop-2-en-1-yl)-2-azetidinone (5.85 g) and sodium nitride (0.063 g) in dimethylsulphoxide (58 cc.) is stirred for 15 minutes under a nitrogen atmosphere at a temperature of between 21°and 23°C. The reaction mixture is poured into water which is saturated with sodium chloride and to which crushed ice has been added (500 cc.) and the resulting mixture is stirred for 10 minutes; the solid which appears is filtered off, washed with distilled water (3 times 25 cc.) and dissolved in ethyl acetate (200 cc.). The solution obtained is washed with a saturated solution of sodium bicarbonate (twice 50 cc.) and distilled water (twice with 50 cc.), dried over sodium sulphate and evaporated under reduced pressure (12 mm Hg) at 30°C. The residue obtained is taken up in a mixture of toluene (30 cc.) and diethyl ether (30 cc.); the resulting mixture is stirred for 2 hours at a temperature of about 20°C and then the crystalline product which has appeared is filtered off and dried. 3-Methyl-8-oxo-7-phenylacetamido-2-trichloroethoxycarbonyl-5-thia-1-aza-bicyclo[4,2,0]oct-2-ene (1.80 g), which melts at 161°C, is thus obtained.

The filtrate is concentrated to dryness under reduced pressure (12 mm Hg) at 30°C and the residue is taken up in methylene chloride (50 cc.). The solution obtained is chromatographed on a column of silica (40 g) (0.06–0.20 mm, pH neutral; diameter of the column: 2.5 cm, height: 20 cm), and elution is carried out using methylene chloride and collecting 50 cc. fractions. Fractions 6 to 15 are combined and concentrated to dryness under reduced pressure (12 mm Hg) at 30°C. The residue is taken up in a mixture of toluene (15 cc.) and diethyl ether (15 cc.) and then the resulting mixture is stirred for 2 hours at a temperature of about 20°C. After filtration and drying, 3-methyl-8-oxo-7-phenylacetamido-2-trichloroethoxycarbonyl-5-thia-1-aza-bicyclo[4,2,0]oct-2-ene (0.65 g), which melts at 162°C, is again obtained.

4-(5-Methyl-2-thiadiazolyl-dithio)-3-phenylacetamido-1-(1-trichloroethoxycarbonyl-2-methyl-prop-2-en-1-yl)-2-azetidinone used as the starting product can be prepared in the following way:

A solution of trichloroethyl 6β-phenylacetamido-penicillanate 1β-oxide (9.62 g) and 2-mercapto-5-methyl-1,3,4-thiadiazole (2.64 g) in toluene (150 cc.) is heated under reflux for 2 hours, and the water formed during the reaction is removed as it is formed by passing the condensate over calcium chloride before reintroducing it into the reaction mixture. The solvent is evaporated under reduced pressure (12 mm Hg) at 40°C and then the oily product is taken up in diethyl ether (100 cc) in order to bring about crystallisation.

After filtration and drying, 4-(5-methyl-2-thiadiazolyl-dithio)-3-phenylacetamido-1-(1-trichloroethoxycarbonyl-2-methyl-prop-2-en-1-yl)-2-azetidinone (9.3 g) is obtained in the form of a white crystalline solid which melts at 109°–110°C and the characteristics of which are as follows: Rf = 0.39 [silica gel; chloroform/ethyl acetate (50/50 by volume)]

Optical rotation: $[\alpha]_D^{20} = -48.4°$ (c = 1.09, chloroform)

NMR spectrum (CDCl$_3$): 2.0 (S, 3H) —CH$_3$; 2.76 (S, 3H) —CH$_3$ (heterocyclic); 3.75 (S, 2H) —CH$_2$CH—; 4.80 (AB, J = 12, 2H) —COOCH$_2$CCl$_3$; 5.05 (S, 1H) —CHCOO; 5.15 (S wide, 1H) and 5.22 (S large, 1H) =CH$_2$; 5.4 (DD, J= 8 and 4, 1H) —H in the 3-position; 5.6 (D, J = 4, 1H) —H in the 4-position; 7.05(D, J = 8, 1H) —CONH—; and 7.35 (S, 5H) C$_6$H$_5$—.

Infra-red spectrum (determination using a solution in bromoform): 3420, 1680 and 1510: amide; 1775: carbonyl of the β-lactam; and 1760: ester.

EXAMPLE 9

A mixture of 4-(1-methyl-5-tetrazolyl-dithio)-3-phenylacetamido-1-(1-trichloroethoxycarbonyl-2-methylprop-2-en-1-yl)-2-azetidinone (8.7 g) and sodium nitride (97.5 mg) in anhydrous dimethylsulphoxide (80 cc.) is stirred for 30 minutes under a nitrogen atmosphere at a temperature of +23°C. The reaction mixture is poured into water which is saturated with sodium chloride and to which crushed ice has been added (750 cc.) and then the resulting mixture is extracted with ethyl acetate (3 times 200 cc.). The organic extracts are washed with water (250 cc.), a saturated solution of sodium bicarbonate (250 cc.) and distilled water (4 times 250 cc.), and then dried over sodium sulphate, filtered and concentrated to dryness under reduced pressure (12 mm Hg) at 25°C. The residue obtained is dissolved in methylene chloride (80 cc.) and the solution obtained is chromatographed on a column of silica (100 g) (0.06–0.20 mm, pH neutral; diameter of the column: 3.5 cm, height: 16 cm). Elution is carried out using methylene chloride, collecting 100cc. fractions. Fractions 5 to 14 are combined; after evaporation under reduced pressure (12 mm Hg) at +30°C, a light maroon solid (2.3 g) is obtained which is recrystallised from toluene (30 cc.). 3-Methyl-8-oxo-7-phenylacetamido-2-trichloroethoxycarbonyl-5-thia-1-aza-bicyclo[4,2,0]oct-2-ene (1.75 g) is thus obtained in the form of white crystals which melt at 162°C.

4-(1-Methyl-5-tetrazolyl-dithio)-3-phenylacetamido-1-(1-trichloroethoxycarbonyl-2-methyl-prop-2-en-1-yl)-2-azetidinone used as the starting product can be prepared in the following way.

A solution of trichloroethyl 6β-phenylacetamido-penicillanate 1β-oxide (28.86 g) and 5-mercapto-1-methyl-tetrazole (6.96 g) in toluene (800 cc.) is heated under reflux for 3 hours, and the water formed during the reaction is removed as it is formed by passing the condensate over calcium chloride before reintroducing it into the reaction mixture. The solvent is evaporated under reduced pressure (12 mm Hg) at 40°C; the residue obtained is dissolved in chloroform (50 cc.) and the solution obtained is chromatographed on a column of silica (400 g) (0.06–0.20 mm, pH neutral; diameter of the column: 4.8 cm., height: 55 cm.). Elution is carried out using chloroform, collecting 250 cc. fractions. Fractions 10 to 17 are combined and concentrated to dryness under reduced pressure (12 mm Hg) at 40°C. 4-(1-Methyl-5-tetrazolyl-dithio)-3-phenylacetamido-1-(1-trichloroethoxycarbonyl-2-methyl-prop-2-en-1-yl)-2-azetidinone (17.4 g.) is obtained in the form of a colourless pastelike product, the characteristics of which are as follows: Rf = 0.50 [silica gel; chloroform/ethyl acetate (50/50 by volume)].

NMR spectrum (CDCl$_3$): 2.0 (S, 3H) —CH$_3$; 3.62 (S, 2H) —CH$_2$CO—; 3.98 (S, 3H) —CH$_3$ (heterocyclic); 4.8 (AB, J = 12, 2H) —COOCH$_2$CCl$_3$; 4.9 to 5.4 (hump, 4H) —CH$_2$—,—CHCOO— and —H in the 3-position; 5.65 (D, J = 4.5, 1H) —H in the 4-position; 6.9 (D, J = 8, 1H) —CONH—; and 7.30 (S, 5H) C$_6$H$_5$—.

Infra-red spectrum (determination using a solution in bromoform):3400, 1670 and 1505: amide; 1770: carbonyl of the β-lactam; and 1755: ester.

EXAMPLE 10

A mixture of 4-(5-methyl-2-thiadiazolyl-dithio)-3-phenylacetamido-1-(1-trichloroethoxycarbonyl-2-methylprop-en-1-yl)-2-azetidinone (5.95 g.) and sodium fluoride (0.42 g.) in dimethylsulphoxide (60 cc.) is stirred at a temperature of 20°C for 12 hours. The reaction mixture is then poured into chilled water (250 cc.) and the resulting mixture is stirred for 15 minutes. The precipitate is filtered off and washed with water (4 times 50 cc.) and is then dissolved in ethyl acetate (250 cc.). The organic phase is washed with distilled water (5 times 100 cc.), dried over magnesium sulphate and concentrated to dryness under reduced pressure (12 mm Hg) at 30°C. The residue is taken up in 1,2-dichloroethane (50 cc.) and the solution is chromatographed on a column of silica (40 g.) (pH neutral, 0.06–0.2 mm.; diameter of the column: 2.5 cm., height: 17 cm.). Elution is carried out using 1,2-dichloroethane, collecting 50 cc. fractions. Fractions 6 to 25 are combined and concentrated to dryness under reduced pressure (12 mm Hg) at 30°C. A solid (0.9 g.) is obtained which, when crystallised from a mixture of toluene and ether (10/10 by volume) (10 cc.), yields 3-methyl-8-oxo-7-phenylacetamido-2-trichloroethoxycarbonyl-5-thia-1-aza-bicyclo[4,2,0]oct-2-ene (0.35 g.) in the form of a crystalline white solid which melts at 162°C.

EXAMPLE 11

A solution of 4-(5-methyl-2thiadiazolyldithio)-3-phenylacetamido-1-(1-trichloroethoxycarbonyl-2-methyl-prop-2-en-1-yl)-2-azetidinone (5.95 g.) in 2-N-methylpyrrolidone (60 cc.) is stirred for 1 hour at a temperature of 20°C. The reaction mixture is poured into chilled water (250 cc.) and the resulting solution is stirred for 15 minutes. The precipitate is filtered off, washed with water (4 times 50 cc.) and dissolved in ethyl acetate (250 cc.). The solution obtained is washed successively with distilled water (100 cc.), a chilled saturated solution of sodium bicarbonate (twice 100 cc.) and distilled water (4 times 50 cc.), dried over magnesium sulphate and concentrated to dryness under reduced pressure (12 mm Hg) at 30°C.

The residue is dissolved in 1,2-dichloroethane (50 cc.) and the solution is chromatographed on a column of silica (40 g.) (pH neutral, 0.06–0.2 mm.; diameter of the column: 2.5 cm., height: 17 cm.). Elution is carried out using 1,2-dichloroethane, collecting 50 cc. fractions. Fractions 4 to 25 are combined and concentrated to dryness under reduced pressure (12 mm Hg) at 30°C. A solid (2.2 g.) is obtained which, when crystallised from a mixture of toluene and ether (10/10 by volume) (20 cc.), yields 3-methyl-8-oxo-7-phenylacetamido-2-trichloroethoxycarbonyl-5-thia-1-aza-bicyclo[4,2,0]oct-2-ene (1.3 g.) in the form of a crystalline white solid which melts at 162°C.

EXAMPLE 12

7-ADCA is prepared from 3-methyl-8-oxo-7-trichloroacetamido-2-trichloroethoxycarbonyl-5-thia-1-aza-bicyclo[4,2,0]oct-2-ene, using the following procedure:

a. Zinc in the form of a fine powder (1.16 g.) is added all at once to a solution, cooled to +3°C, of 3-methyl-8-oxo-7-trichloroacetamido-2-trichloroethoxycarbonyl-5-thia-1-aza-bicyclo[4,2,0]oct-2-ene (0.982 g.) in dimethylformamide (25 cc.) and acetic acid (1.5 cc.). The mixture is stirred for 5 minutes at +3°C and is then allowed to return over the course of 2 hours to a temperature of about 20°C.

The reaction mixture is filtered, the solid is washed with dimethylformamide (3 times 25 cc.) and the filtrate is poured into chilled water (200 cc.). The resulting mixture is acidified by adding normal hydrochloric acid (12 cc.) and is extracted with ethyl acetate (3 times 250 cc.). The organic phase is washed with water (3 times 100 cc.), dried over sodium sulphate, filtered and concentrated under reduced pressure (12 mm Hg) at 30°C. The residue is taken up in petroleum ether (boiling point = 40°–60°C) (twice 50 cc.) and crystallises in the form of a white solid. The solid is filtered off, washed with petroleum ether (twice 20 cc.) and dried. 2-Carboxy-7-chloroacetamido-3-methyl-8-oxo-5-thia-1-aza-bicyclo[4,2,0]oct-2-ene (560 mg.) is obtained, the characteristics of which are as follows: Rf = 0.64 [silica gel; acetone/acetic acid (95/5 by volume)]

Analysis: calculated %: C 41.25, H 3.79, N 9.65, S 11.00, Cl 12.40. Found: 41.45, 3.95, 9.8, 10.0, 12.6.

Optical rotation: $[\alpha]_D^{20} = +127°$ (c = 0.96; dimethylformamide)

NMR spectrum (DMSO $d_6$): 2.03 (S, 3H) —$CH_3$; 3.35 and 3.55 (AB, 2H) —$SCH_2$—; 4.13 (S, 2H) $ClCH_2$—; 5.05 (D, J = 5, 1H) —H in the 6-position; 5.58 (DD, J = 5 and 8.5, 1H) —H in the 7-position; and 9.05 (D, J = 8.5, 1H) —CONH—.

Infra-red spectrum (determination using a solution in bromoform) 3315, 1675 and 1540: amide; 3200 to 2300 and 1710; carboxylic acid; 1765: carbonyl of the β-lactam; 1620: ethylenic double bond.

b. A suspension of 2-carboxy-7-chloroacetamido-3-methyl-8-oxo-5-thia-1-aza-bicyclo[4,2,0]oct-2-ene (290.5 mg.) in water (8 cc.) is brought to pH 7 by adding normal sodium hydroxide solution (1 cc.). Thiourea (114 mg.) is added to the solution obtained and the whole is stirred at 30°C for 48 hours.

The reaction mixture is then left at 4°C for 24 hours, the precipated solid is collected by filtration and dried to yield 7-amino-2-carboxy-3-methyl-8-oxo-5-thia-1-aza-bicyclo[4,2,0]oct-2-ene (150 mg.; 7-ADCA) as a white solid, the characteristics of which are as follows: Rf = 0.40 [silica gel; 0.5 M solution of sodium chloride]

NMR spectrum ($D_2O$/NaHCO$_3$): 2.02 (S, 3H) —$CH_3$; 3.33 and 3.70 (AB, J = 18, 2H) —$SCH_2$—; 5.16 (D, J = 4.5, 1H) —H in the 6-position; and 5.53 (D, J = 4.5, 1H) —H in the 7-position.

Infra-red spectrum (KBr tablet): 2850 to 1880 and 1615: amine (internal salt); 1795: carbonyl of the β-lactam; 1645: ethylenic double bond and 1530: carboxyl (internal salt).

EXAMPLE 13

7-ADCA is prepared from 2-p-methoxybenzyloxycarbonyl-3-methyl-8-oxo-7-trichloroacetamido-5-thia-1-aza-bicyclo[4,2,0]oct-2-ene using the following procedure:

a. 2-p-Methoxybenzyloxycarbonyl-3-methyl-8-oxo-7-trichloroacetamido-5-thia-1-aza-bicyclo[4,2,0]oct-2-ene (150 mg.) is added, all at once and with stirring, to trifluoroacetic acid (5 cc.) cooled to +10°C. The mixture is stirred for 30 minutes at a temperature between +10° and +15°C and is then concentrated to dryness under reduced pressure (0.05 mm Hg) without heating. The pink-colored residue is taken up in ethyl aceate (100 cc.) and the resulting mixture is concentrated to dryness under reduced pressure (12 mm Hg) at 30°C. The residue obtained is dissolved in diethyl ether (20 cc.). Petroleum ether (boiling point = 40°–60°C) (100 cc.) is added and the mixture is left for 2 hours at +3°C and filtered. 2-Carboxy-3-methyl-8-oxo-7-trichloroacetamido-5-thia-1-aza-bicyclo[4,2,0]oct-2-ene (105 mg.) is thus collected, the characteristics of which are as follows: Rf = 0.71 [silica gel; acetone/acetic acid (95/5 by volume)]

NMR spectrum [CDCl$_3$/DMSO $d_6$ (99/1 by volume)]: 2.20 (S, 3H) —$CH_3$; 3.40 (AB, J = 14, 2H) —$SCH_2$—; 5.05 (D, J = 4.5, 1H) —H in the 6-position; 5.60 (DD, J = 4.5 and 9, 1H) —H in the 7 position; 6.80 (hump) —COOH and DOH; and 7.82 (D, J= 9, 1H) —NH—.

Infra-red spectrum (determination using a solution in bromoform): 3395, 1715 and 1505: amide; 3550 to 2300 and 1710: carboxylic acid; 1775: carbonyl of the β-lactam; 1625: ethylenic double bond; 1365: gem-dimethyl; 810: trichloromethyl.

The characteristics of the infra-red and NMR spectra of this product are identical to those of spectra obtained from an authentic sample of 7-ADCA.

b. Sodium borohydride (78 mg.) is added in small portions and over the course of 30 minutes to a solution, cooled to +5°C, of 2-carboxy-3-methyl-8-oxo-7-trichloroacetamido-5-thia-1-aza-bicyclo[4,2,0]oct- 2-ene (360 mg.) in absolute ethanol (25 cc.). The mixture is then stirred for 1 hour at +5°C.

The mixture is poured into water (20 cc.) to which crushed ice and normal hydrochloric acid (4 cc.) have been added. The resulting mixture is extracted with ethyl acetate (3 times 50 cc.) and the pH of the aqueous phase is adjusted to 3.7 by adding normal sodium hydroxide solution. After 24 hours at a temperature of about +2°C, a product crystallises. After filtering off the crystals and drying them, 7-amino-2-carboxy-3-methyl-8-oxo-5-thia-1-aza-bicyclo[4,2,0]oct-2-ene (120 mg.) is obtained in the form of a white solid. Rf = 0.40 [silica gel; 0.5 M solution of sodium chloride].

The characteristics of the infra-red and NMR spectra of this product are identical to those of spectra obtained from an authentic sample of 7-ADCA.

We claim:

1. A 7-trichloroacetamido-3-desacetoxy-cephalosporanic acid of the formula:

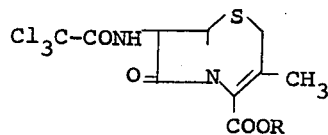

in which R is alkyl of 1 to 4 carbon atoms, unsubstituted or substituted by halogen, benzyl, unsubstituted or substituted by nitro or alkoxy of 1 to 4 carbon atoms, or phenacyl.

2. A compound as claimed in claim 1, in which R is methyl, tertiary butyl, 2,2,2-trichloroethyl, benzyl, p-methoxybenzyl, p-nitrobenzyl or phenacyl.

3. A compound as claimed in claim 1 which is 3-methyl-8-oxo-7-trichloroacetamido-2-trichloroethoxycarbonyl-5-thia-1-aza-bicyclo[4,2,0]oct-2-ene.

4. A compound as claimed in claim 1, which is 2-p-methoxybenzyloxycarbonyl-3-methyl-8-oxo-7-trichloroacetamido-5-thia-1-aza-bicyclo[4,2,0]oct-2-ene.

* * * * *